United States Patent
Tuch et al.

(10) Patent No.: US 11,963,807 B2
(45) Date of Patent: Apr. 23, 2024

(54) TETHERED LAPAROSCOPIC PROBE

(71) Applicant: LIGHTPOINT MEDICAL, LTD, Chesham (GB)

(72) Inventors: David Tuch, Chesham (GB); Kunal Vyas, Chesham (GB); Stewart Forbes, Chesham (GB); Gavin Ryan, Chesham (GB); Phil Marsden, Chesham (GB)

(73) Assignee: Lightpoint Surgical Ltd., Amersham (GB)

( * ) Notice: Subject to any disclaimer, the term of this patent is extended or adjusted under 35 U.S.C. 154(b) by 864 days.

(21) Appl. No.: 16/986,121

(22) Filed: Aug. 5, 2020

(65) Prior Publication Data
US 2020/0367841 A1 Nov. 26, 2020
US 2021/0361247 A9 Nov. 25, 2021

Related U.S. Application Data

(63) Continuation of application No. PCT/GB2019/050305, filed on Feb. 13, 2019.

(30) Foreign Application Priority Data

Feb. 6, 2018 (GB) ..................................... 1801926

(51) Int. Cl.
*A61B 6/00* (2006.01)
*A61B 1/00* (2006.01)
(Continued)

(52) U.S. Cl.
CPC ........ *A61B 6/4057* (2013.01); *A61B 1/00114* (2013.01); *A61B 1/00124* (2013.01);
(Continued)

(58) Field of Classification Search
CPC ....... A61B 6/4057; A61B 6/107; A61B 6/425; A61B 6/4258; A61B 6/4241; A61B 6/44;
(Continued)

(56) References Cited

U.S. PATENT DOCUMENTS 4,405,861 A 9/1983 Giacchetti et al.
4,959,547 A 9/1990 Carroll et al.
(Continued)

FOREIGN PATENT DOCUMENTS

CN 1545395 A 11/2004
CN 206684310 U 11/2017
(Continued)

OTHER PUBLICATIONS

Kotzassarlidou et al. "Practical Considerations in Selecting and Using Intraoperative Gamma Probes". Nuclear Instruments and Methods in Physics Research Section A. Published by Elsevier. vol. 527, pp. 110-112 (2004).
(Continued)

*Primary Examiner* — Peter Luong
(74) *Attorney, Agent, or Firm* — Jeffrey G. Sheldon; Cislo & Thomas LLP

(57) ABSTRACT

A tethered laparoscopic probe is provided, the tethered laparoscopic probe for deployment through a trocar into a cavity of a subject to detect gamma radiation from a radiopharmaceutical administered to the subject. The laparoscopic probe comprises a probe head shaped for insertion through the trocar and configured to be freely moveable within the cavity. The probe head comprises an elongate casing comprising radiation shielding for inhibiting gamma radiation from passing through the probe head, the radiation shielding having a detection aperture for admitting gamma radiation. The probe head further comprises a gamma radiation detector arranged within the casing, the gamma radiation detector configured to detect gamma radiation through the detection aperture of the casing. The probe head further comprises means for, in use, facilitating the localization of a source of radiation from the radiopharmaceutical within the cavity. The laparoscopic probe further comprises a tether (Continued)

coupled to the probe head and for, in use, tethering the probe head through the trocar.

20 Claims, 13 Drawing Sheets

(51) Int. Cl.
    *A61B 1/313*     (2006.01)
    *A61B 6/10*     (2006.01)
    *A61B 6/40*     (2024.01)
    *A61B 6/42*     (2024.01)
    *G01T 1/20*     (2006.01)
    *G01T 1/24*     (2006.01)

(52) U.S. Cl.
    CPC ............ *A61B 1/3132* (2013.01); *A61B 6/107* (2013.01); *A61B 6/425* (2013.01); *A61B 6/4258* (2013.01); *G01T 1/2018* (2013.01); *G01T 1/24* (2013.01)

(58) Field of Classification Search
    CPC ..... A61B 6/06; A61B 6/4452; A61B 1/00114; A61B 1/00124; A61B 1/3132; A61B 2017/00079; G01T 1/2018; G01T 1/24
    See application file for complete search history.

(56) References Cited

U.S. PATENT DOCUMENTS

| | | |
|---|---|---|
| 5,766,234 A | 6/1998 | Chen et al. |
| 6,236,880 B1 | 5/2001 | Raylman et al. |
| 6,484,050 B1 | 11/2002 | Carroll et al. |
| 2006/0106306 A1 | 5/2006 | Essner et al. |
| 2007/0221853 A1 | 9/2007 | Joung |
| 2014/0309529 A1 | 10/2014 | O'Neill et al. |
| 2016/0266260 A1* | 9/2016 | Preston .................. G01T 1/208 |

FOREIGN PATENT DOCUMENTS

| | | |
|---|---|---|
| DE | 102014108055 A1 | 12/2015 |
| EP | 1596223 | 11/2005 |
| JP | 0249185 A | 2/1990 |
| WO | 9015346 A2 | 12/1990 |
| WO | WO9925248 | 5/1999 |
| WO | 2015185665 A1 | 12/2015 |

OTHER PUBLICATIONS

UK Application No. GB1801926.5. Examination Report dated Feb. 15, 2021. 6 pages.

Daghighian, et al., "Intraoperative Beta Probe: A Device for Detecting Tissue Labeled with Positron or Electron Emitting Isotopes During Surgery", Medical Physics, vol. 21, No. 1, Jan. 1994, pp. 153-157.

GB1801926.5, "Combined Search and Examination Report", dated Jul. 23, 2018, 10 pages.

PCT/GB2019/050305, "International Search Report", dated Jun. 14, 2019, 5 pages.

Chinese Application No. 201980012190. Machine Translation of First Office Action dated Dec. 12, 2023. 22 pages.

\* cited by examiner

TETHERED LAPAROSCOPIC PROBE

CROSS-REFERENCES TO RELATED APPLICATIONS

This application claims priority to and is a continuation of International Patent Application No. PCT/GB2019/050305, filed Feb. 13, 2019; which claims priority from GB Patent Application No. 1801926.5, filed Feb. 6, 2018, the entire contents of which are hereby incorporated by reference in their entirety for all purposes.

BACKGROUND OF THE INVENTION

Laparoscopic surgery, also called minimally-invasive surgery or keyhole surgery, is a surgical technique in which operations are performed using a small incision (usually 0.5-1.5 cm) in the body of a subject. Laparoscopic surgery provides a host of clinical benefits over open surgery, for example pain and hemorrhaging are reduced due to smaller incisions, and recovery times for the patient are reduced.

In order to perform laparoscopic surgery on a subject, a small incision is made in the body of the subject and a trocar is placed into the incision. A trocar is a medical device that acts as a portal for the subsequent placement of other instruments into a cavity of the subject for use in the surgery. The size of the trocar, for example the diameter of the trocar, provides a limit on the size of the instrument(s) that can be used in the laparoscopic surgery, as the instruments need to be able to pass through the trocar into the subject. For some types of laparoscopic surgeries, multiple instruments may be required—if these instruments are required at the same time and each take up a port, then multiple incisions may be required, leading to patient discomfort and slower patient recovery times.

Sometimes, a laparoscopic gamma probe may be used for radioguided laparoscopic procedures. A subject may receive a radiopharmaceutical in advance of surgery, the radiopharmaceutical designed to locate abnormal tissue such as tumors in the subject and to emit radiation detectable by a probe. A radiopharmaceutical is a drug that can be used for diagnostic or therapeutic purposes and comprises a radioisotope bonded to a molecule. The radiopharmaceutical conveys the isotope to specific organs, tissues or cells, and is selected for its properties and purpose. Many radiopharmaceuticals are known in the art and are used for radioguided surgery and other procedures. A laparoscopic gamma probe, which typically comprises a gamma radiation detector supported by a rigid rod, may be inserted through a trocar into a cavity of the subject in an attempt to locate the source of the radiation and thereby locate any abnormal tissue. However, such probes have limited maneuverability within the cavity due to the restriction of movement of the rigid rod within the trocar. Furthermore, such laparoscopic probes would use up an entire trocar, and so further incisions in the subject would be required if further surgical tools are required for the surgery.

The present application provides solutions to overcome problems such as those described above.

SUMMARY OF THE INVENTION

The present disclosure relates to laparoscopic probes. In particular, the present disclosure relates to a tethered laparoscopic probe to be inserted via a trocar, after which another laparoscopic tool can be inserted into the trocar to manipulate the probe. The laparoscopic probe(s) described herein are suitable for detecting radiation emitted from a radiopharmaceutical administered to a subject ahead of a procedure.

According to an aspect of the invention, a tethered laparoscopic probe is provided. The tethered laparoscopic probe is for deployment through a trocar into a cavity of a subject to detect gamma radiation from a radiopharmaceutical administered to the subject. The laparoscopic probe comprises a probe head shaped for insertion through the trocar and configured to be freely moveable within the cavity. The probe head comprises an elongate casing comprising radiation shielding for inhibiting gamma radiation from passing through the probe head, the radiation shielding having a detection aperture for admitting gamma radiation. The probe head further comprises a gamma radiation detector arranged within the casing, the gamma radiation detector configured to detect gamma radiation through the detection aperture of the casing. The probe head further comprises means for, in use, facilitating the localization of a source of radiation from the radiopharmaceutical within the cavity. The laparoscopic probe further comprises a tether coupled to the probe head and for, in use, tethering the probe head through the trocar.

By providing such a tethered laparoscopic probe, the laparoscopic probe may be deployed through a port of a trocar and, in use, not take up the entire capacity of the port. Accordingly, further instrument(s) may be used with the same trocar port while the laparoscopic probe is deployed. Further advantageously, in comparison to traditional laparoscopic probes which comprise a rigid rod like structure limiting control of a detector head to four degrees of freedom, a tethered laparoscopic probe as described herein may, in use, have six degrees of freedom.

As the laparoscopic probe is for deployment into a cavity, it is necessary that the probe head is small enough to pass through a port of a trocar, which may be, for example, 12 mm in diameter. Such a restriction on the size of the probe head means that, once deployed, gamma radiation may pass through the side or rear of the probe head and setting off the gamma radiation detector, even with radiation shielding. To provide means for, in use, facilitating the localization of a source of radiation from the radiopharmaceutical in the cavity, is therefore advantageous as it allows a user to locate the source of gamma radiation. As will be described further below, such means may thereby provide a greater assurance to the user that detections are the result of radiation passing through the detection aperture of the laparoscopic probe as opposed to through the side or rear. By providing means for, in use, facilitating the localization of a source of radiation from the radiopharmaceutical within the cavity, a user of the probe is able to locate the affected tissue efficiently.

The gamma radiation detector may comprise a scintillator configured to scintillate, in use, in response to received gamma radiation. The gamma radiation detector may further comprise a photodetector to detect the scintillated light from the scintillator. The photodetector may comprise a silicon photomultiplier ("SiPM"). The photodetector may comprise an avalanche photodiode ("APD"). The scintillator may comprise Thallium activated Cesium Iodide, CsI:Tl.

The radiation shielding may have a thickness, and the scintillator may have a radius, and the thickness of the radiation shielding and the radius of the scintillator may be selected such that, in use, the ratio of the gamma radiation permeating through the radiation shielding that is detected by the gamma detection means to the gamma radiation incident on the radiation shielding is less than or equal to 1:1000, and such that, in use, the sensitivity of the gamma detection means to gamma radiation incident through the detection aperture is maximized.

By providing such radiation shielding and scintillator, the ability of the probe to locate the source of radiation is greatly improved as such a ratio is suitable to assure a user that the likelihood that any detected radiation passed through the detection aperture of the laparoscopic probe is high compared to the likelihood that the radiation passed through any other part of the probe head 102.

The gamma radiation detector may comprise a semiconductor gamma radiation detector. The semiconductor radiation detector may comprise Cadmium Zinc Telluride, CZT.

The means for facilitating the localization of a source of radiation from the radiopharmaceutical within the cavity may comprise a beta radiation detector arranged within the casing, between the detection aperture and the gamma radiation detector, and configured to detect beta radiation through the detection aperture of the radiation shielding. That is, the laparoscopic probe may comprise a probe head shaped for insertion through the trocar and configured to be freely moveable within the cavity, the probe head comprising: an elongate casing comprising radiation shielding for inhibiting gamma radiation from passing through the probe head, the radiation shielding having a detection aperture for admitting gamma radiation; a gamma radiation detector arranged within the casing, the gamma radiation detector configured to detect gamma radiation through the detection aperture of the casing; and a beta radiation detector arranged within the casing, between the detection aperture and the gamma radiation detector, and configured to detect beta radiation through the detection aperture of the radiation shielding.

The beta radiation detector may comprise a scintillator configured to scintillate, in use, in response to received beta radiation. The beta radiation detector may further comprise a photodetector to detect the scintillated light from the scintillator. The scintillator configured to scintillate in response to received beta radiation may comprise cesium iodide, CsI. The scintillator configured to scintillate in response to received beta radiation may comprise fluorophore doped vinyltoluene.

By providing such a beta radiation detector, the laparoscopic probe is enabled to pick up further signatures of a radioisotope. Furthermore, charged particles from radiopharmaceuticals do not travel far through tissue and so, using a beta radiation detector, one may determine that the radiation source is close when charged particles are detected.

The laparoscopic probe may be arranged to communicate a composite signal, the composite signal representative of detections of beta radiation and detections of gamma radiation. The laparoscopic probe may be switchable between a first mode, in which the probe head is configured to communicate a first signal representative of a detection of gamma radiation, and a second mode, in which the probe head is configured to communicate a second signal representative of a detection of beta radiation.

The means for facilitating the localization of a source of radiation from the radiopharmaceutical within the cavity may comprise a mechanism for moving the gamma detector relative to the radiation shielding of the casing to adjust the field of view of the gamma detector through the aperture. The gamma radiation detector may be adjustable in use. Advantageously, such a dynamically adjustable gamma radiation detector enables a user to obtain multiple images with different fields of view in order to localize the source of the radiation within the cavity. That is, the laparoscopic probe may comprise a probe head shaped for insertion through the trocar and configured to be freely moveable within the cavity, the probe head comprising: an elongate casing comprising radiation shielding for inhibiting gamma radiation from passing through the probe head, the radiation shielding having a detection aperture for admitting gamma radiation; a gamma radiation detector arranged within the casing, the gamma radiation detector configured to detect gamma radiation through the detection aperture of the casing; and a mechanism for moving the gamma detector relative to the radiation shielding of the casing to adjust the field of view of the gamma detector through the aperture.

The gamma radiation detector may comprise a first scintillator configured to scintillate, in use, in response to received gamma radiation; and a photodetector to detect the scintillated light from the scintillator; and the means for facilitating the localization of a source of radiation from the radiopharmaceutical within the cavity may comprise a second scintillator configured to scintillate, in use, in response to received gamma radiation, the second scintillator arranged between the first scintillator and the detection aperture of the radiation shielding. The means for facilitating the localization of a source of radiation from the radiopharmaceutical within the cavity may further comprise a second photodetector to detect the scintillated light from the second scintillator, the second photodetector arranged between the first scintillator and the second scintillator. Advantageously, by providing two such gamma radiation detectors, the laparoscopic probe is capable of "active collimation". The signals from both detectors may be used to extract directional information on detected gamma radiation, and accordingly the signal to noise ratio of the laparoscopic probe is greatly increased.

The means for facilitating the localization of a source of radiation from the radiopharmaceutical within the cavity may comprise deployable radiation shielding having a deployed configuration and an undeployed configuration. In the undeployed configuration, the deployable radiation shielding may be arranged such that the probe head is insertable through the trocar. In the deployed configuration, the deployable radiation shielding may be arranged to further inhibit gamma radiation from passing through the probe head. That is, the laparoscopic probe may comprise a probe head shaped for insertion through the trocar and configured to be freely moveable within the cavity, the probe head comprising: an elongate casing comprising radiation shielding for inhibiting gamma radiation from passing through the probe head, the radiation shielding having a detection aperture for admitting gamma radiation; a gamma radiation detector arranged within the casing, the gamma radiation detector configured to detect gamma radiation through the detection aperture of the casing; and deployable radiation shielding having a deployed configuration and an undeployed configuration.

As discussed above, if the radiation shielding on the probe head is too thin then gamma radiation may penetrate through the outer casing of the probe head and be detected by the detector, thereby reducing one's ability to localize the radiation source. By providing deployable shielding the probe head may be passed through the (limited diameter) port of the trocar into the cavity, and then the deployable shielding may be deployed to thicken the amount of radiation shielding that gamma radiation would need to pass through to reach the detector, thereby reducing the gamma radiation penetrating through, for example, the rear of side of the probe head.

The deployable radiation shielding may be separate to the radiation shielding of the casing. The deployable radiation shielding may comprise rigid, foldable sheeting. The deployable radiation shielding may comprise a deformable outer surface. The deployable radiation shielding may comprise a filler material. In the deployed configuration, the filler material may fill a void between the deformable outer surface and the casing such that the shielding depth is greater than in the undeployed configuration. The filler material may comprise tungsten beads or powder.

The deployable radiation shielding may be moveable between the undeployed configuration and the deployed configuration using surgical tools.

The tether may comprise a cable for communicating a signal from the gamma radiation detector from the probe head.

The means for facilitating the localization of a source of radiation from the radiopharmaceutical within the cavity may comprise a tortuous path for an electrical connection through the radiation shielding of the casing to the cable. A tortuous path through the radiation shielding may comprise any suitable path for an electrical connection such that there is no "line of sight" between the radiation detector and the circuitry of the laparoscopic probe. For example, a tortuous path through a layer of radiation shielding may comprise a path for which an entrance to the shielding is offset from an exit from the shielding, for example radially offset and/or azimuthally offset. The tortuous path may include a sinuous path, circuitous path, winding path, serpentine path or even a straight path at an angle relative to a longitudinal axis through the probe head. In this way, from whatever angle radiation approaches the rear of the gamma radiation detector, there should be at least a layer of radiation shielding inhibiting the propagation of that radiation to the detector. Accordingly, the user is provided with greater confidence that detections are the result of gamma radiation passing to the detector via the detection aperture as opposed to via, for example, a piercing in the rear shielding through which electrical connections are made. That is, the laparoscopic probe may comprise a probe head shaped for insertion through the trocar and configured to be freely moveable within the cavity, the probe head comprising: an elongate casing comprising radiation shielding for inhibiting gamma radiation from passing through the probe head, the radiation shielding having a detection aperture for admitting gamma radiation; a gamma radiation detector arranged within the casing, the gamma radiation detector configured to detect gamma radiation through the detection aperture of the casing; and a tortuous path for an electrical connection through the radiation shielding of the casing to the cable.

The tethered laparoscopic probe may further comprise a grip for manipulating the probe head inside the cavity with a surgical tool. The grip may be beveled. The grip may be magnetic.

According to an aspect of the invention, a tethered laparoscopic probe is provided, the tethered laparoscopic probe for deployment through a trocar into a cavity of a subject to detect gamma radiation from a radiopharmaceutical administered to the subject. The laparoscopic probe comprises a probe head shaped for insertion through the trocar and configured to be freely moveable within the cavity. The probe head comprises an elongate casing comprising radiation shielding of a first thickness, the radiation shielding for inhibiting gamma radiation from passing through the probe head, the radiation shielding having a detection aperture for admitting gamma radiation. The probe head further comprises a gamma radiation detector arranged within the casing, the gamma radiation detector configured to detect gamma radiation through the detection region of the casing. The gamma radiation detector comprises a scintillator having a radius, the scintillator configured to scintillate, in use, in response to received gamma radiation. The gamma radiation detector further comprises a photodetector to detect the scintillated light from the scintillator. The thickness of the radiation shielding and the radius of the scintillator are selected such that, in use, the ratio of the gamma radiation permeating through the radiation shielding of the casing that is detected by the gamma detection means to the gamma radiation incident on the radiation shielding is less than or equal to 1:1000, and such that, in use, the sensitivity of the gamma detection means to gamma radiation incident through the detection aperture is maximized. The laparoscopic probe further comprises a tether coupled to the probe head and for, in use, tethering the probe head through the trocar.

According to an aspect of the invention, a method is provided for producing a tethered laparoscopic probe, the tethered laparoscopic probe for deployment through a trocar into a cavity of a subject. The method comprises selecting a radiation shielding thickness and a scintillator radius, based on a known diameter of a trocar and known radiation properties of a radiopharmaceutical when administered to the subject, such that in use the ratio of the gamma radiation permeating through the radiation shielding that is detected by the gamma detector to the gamma radiation incident on the radiation shielding is less than or equal to 1:1000. The method further comprises providing an elongate casing, the elongate casing having a diameter suitable for insertion through the trocar, the casing comprising radiation shielding of the selected radiation shielding thickness. The method further comprises arranging, within the casing, a gamma radiation detector, the gamma radiation detector comprising a scintillator having the selected scintillator radius, the scintillator configured to scintillate, in use, in response to received gamma radiation; and a photodetector to detect the scintillated light from the scintillator. The method further comprises coupling a tether to the probe head.

BRIEF DESCRIPTION OF THE DRAWINGS

Embodiments of the invention are further described hereinafter with reference to the accompanying drawings, in which.

Throughout the description and drawings, like reference numerals refer to like parts.

DETAILED DESCRIPTION OF THE INVENTION

The present disclosure describes tethered laparoscopic probes. Whilst various embodiments are described below, the invention is not limited to these embodiments, and variations of these embodiments may well fall within the scope of the invention which is to be limited only by the appended claims.

Figure 1:
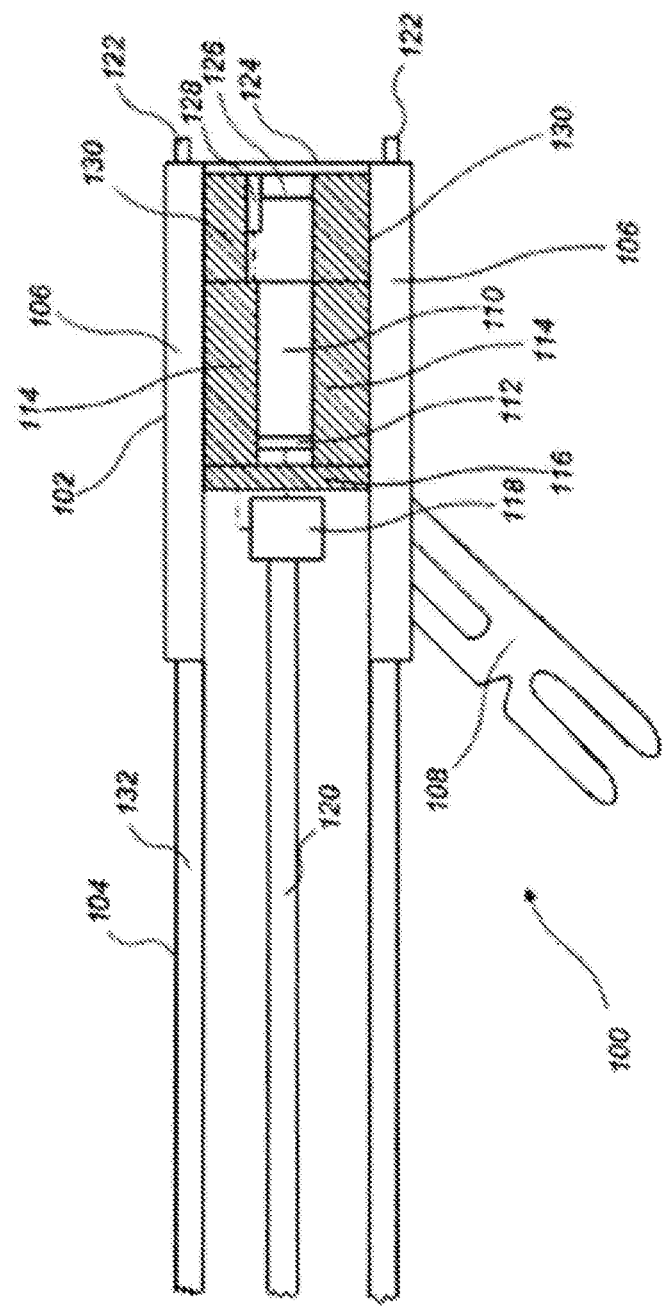
FIG. 1 illustrates a tethered laparoscopic probe according to an embodiment of the invention.

FIG. 1 is a schematic of a tethered laparoscopic probe 100 comprising a probe head 102 and a tether 104 for tethering the probe head 102 through a trocar in use. The probe head 102 is designed for insertion through a trocar into a cavity in the subject under examination (e.g. a patient) and to be freely moveable inside the cavity. The tether 104 of the laparoscopic probe computing device 700 described in detail below). To this end the laparoscopic probe 100 also comprises a deployable/retractable grip 108 for manipulating the probe head 102 of the laparoscopic probe 100 in use with a surgical tool. The grip 108 may be beveled for improved grip, and/or may be magnetic. The grip 108 is retractable such that the diameter or width of the laparoscopic probe 100 is less than the diameter of the trocar port through which the laparoscopic probe head 102 is inserted into the cavity. Typically, a trocar will have a diameter of around 12 mm, although in recent years trocars are often used which have diameters of 10 mm or smaller. The diameter of the probe head, and therefore the components therein, must be small enough to pass through the trocar.

The tether/connecting portion 104 may comprise a biocompatible casing 132 and one or more optical fibers 120 for communicating to the computing device (not shown). The skilled person would appreciate that other laparoscopic probe architectures may be used. Some other examples are provided below.

The probe head 102 comprises an outer casing 106. The outer casing 106 is biocompatible. The outer casing may comprise one or more of tungsten (with a biocompatible coating applied), stainless steel, tantalum and plastic.

Within the probe head 102, there is provided a gamma radiation detector, which in the present example comprises a scintillator 110 and a photodetector 112 for detecting scintillated light from the scintillator 110. The scintillator 110 may be silvered on one or more surfaces, for example on a circumferential face of the scintillator 110 or a face of the scintillator 110 closest to the detection end of the laparoscopic probe 100, to reflect scintillated light towards the photodetector 112. This advantageously results in better signal collection and is also useful for achieving a good energy resolution.

The gamma radiation detector is shielded by rear shielding 116 and side shielding 114. The rear shielding 116 and side shielding 114 may comprise tungsten. The rear shielding 116 and the side shielding 114 are arranged to inhibit gamma radiation from impinging upon the scintillator 110 through, respectively, the rear and side of the probe head 202. Accordingly, it is likely that any scintillated light from the scintillator 110 is likely to have originated from gamma radiation approaching through the detection end of the laparoscopic probe 100. In particular, the radiation shielding defines a detection aperture and channel through which gamma radiation may propagate uninhibited by the shielding.

When scintillated light is detected by the photodetector 112, an electrical signal representative of the detection is sent to the circuitry 118 through a small piercing in the rear shielding 116 via a wire (as indicated by the dashed line in the figure). The circuitry 118 is configured to communicate the detection information along the communication means 120 to a computing device (not shown in FIG. 1).

The probe head 102 further comprises a thin window 124 over the detection aperture and a biocompatible stand-off 122 which keeps the window 124 at least a fixed distance away from a tissue surface in use. The window 124 is permeable to gamma radiation and so permits gamma radiation to pass within the channel formed by the rear shielding 116 and side shielding 114 to be detected. The window may be formed from any suitable material, for example a plastic or polyethylene terephthalate (PET).

The probe head 102 further comprises means for, in use, facilitating the localization of a source of radiation from the radiopharmaceutical within the cavity. In particular, in FIG. 1, the probe head 102 further comprises a charged particle detector, in particular a beta radiation detector. The beta radiation detector is arranged within the outer casing 102, between the detection aperture and the gamma radiation detector and is configured to detect beta radiation through the detection aperture of the radiation shielding.

The beta radiation detector in FIG. 1 comprises a scintillator 126 configured to scintillate, in use, in response to received beta radiation. The scintillator 126 may comprise cesium iodide. The scintillator 126 may comprise fluorophore doped vinyltoluene. As with scintillator 110, scintillator 126 may be silvered on one or more faces.

The beta radiation detector in FIG. 1 further comprises a photodetector 128 to detect scintillated light from the scintillator 126. The photodetector 128 of the present example comprises an avalanche photodiode.

While the photodetector 112 of the gamma radiation detector is arranged behind the scintillator 110 of the gamma radiation detector, the avalanche photodiode 128 is arranged to one side of the scintillator 126. In this way, the avalanche photodiode 128 does not contribute to gamma attenuation, leading to a better reading by the gamma radiation detector.

The beta radiation detector is also shielded by radiation shielding 130. Although the shielding 130 is shown as separate to the shielding 114, the skilled person would appreciate that the radiation shielding 114 and 130 may be combined as one piece of radiation shielding for protecting both the gamma radiation detector and the beta radiation detector.

The avalanche photodiode 128 communicates any detections of scintillated light from the scintillator 126 along a wire (as indicated by the dot-dashed line in the figure) through piercings in the side shielding 114 and the rear shielding 116 to the circuitry 118. The skilled person would appreciate that the wire may take any suitable route to the circuitry, for example a tortuous path around multiple radiation shields.

The circuitry 118 is configured to communicate data relating to detection of gamma radiation to a computing device (not shown), such as computing device 700 described further below. The circuitry 118 is further configured to communicate data relating to detection of charged particles/beta radiation to a computing device such as computing device 700. The circuitry 118 may communicate a composite signal, the composite signal representative of detections of charged particles (e.g. beta radiation) and detections of gamma radiation. Optionally, the laparoscopic probe may be switchable between a first mode, in which the probe head 102 is configured to communicate a first signal representative of a detection of gamma radiation, and a second mode in which the probe head 102 is configured to communicate a second signal representative of a detection of charged particles.

While the beta radiation detector shown in FIG. 1 comprises a scintillator and a photodetector, the skilled person would appreciate that the beta radiation detector may comprise any suitable detector. For example, the inventors have discovered that a complementary metal-oxide-semiconductor (CMOS) sensor is also suitable for detecting charged particles from a radiopharmaceutical. The skilled person would appreciate that while detection of beta radiation has been described, the laparoscopic probe may be used to detect any charged particles.

The laparoscopic probe 100 may comprise further components. For example, the probe 100 may comprise one or more collimators.

The stand-off 122 may or may not be present. If present the stand-off 122 may be of any suitable shape and material. The outer casing 106 may itself perform the function of a stand-off.

In FIG. 1, the beta radiation detector 100 is arranged to detect charged particles from the end of the laparoscopic probe 100. However, other configurations are envisaged, for example the beta radiation detector may be positioned to detect charged particles at the side of the probe head 102. In the embodiment shown in FIG. 1, the gamma radiation detector is also arranged to detect gamma radiation through the detection end of the laparoscopic probe 100. However, the gamma radiation detector may instead be positioned at a different angle to the beta radiation detector. For example, the beta radiation detector may be positioned on the side of the probe head 102 while the gamma detector may be positioned to detect gamma radiation substantially through the detection end of the probe head 102, or vice versa. The data from both detectors may be processed at a computing device (not shown). The laparoscopic probe may comprise further additional radiation sensors.

Figure 2A:
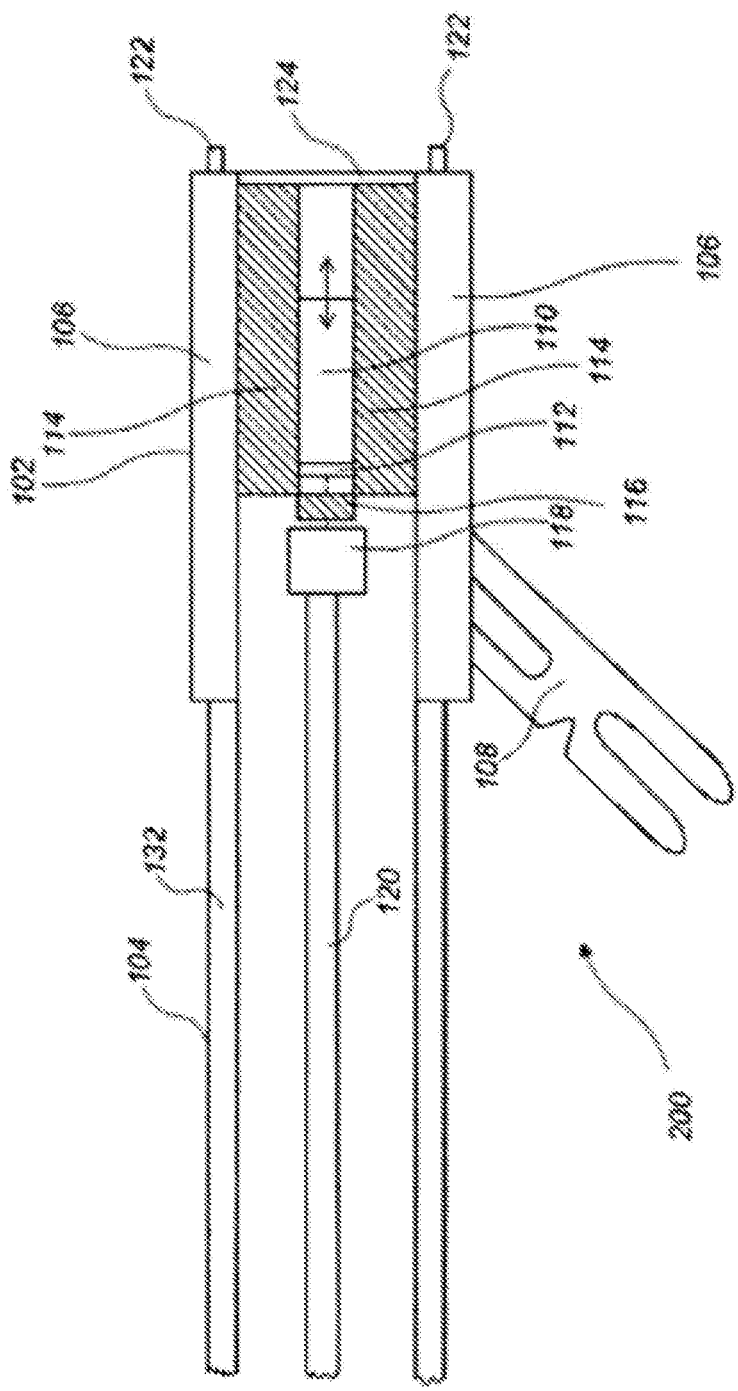
FIG. 2A illustrates a tethered laparoscopic probe according to another embodiment of the invention.

FIG. 2A shows a tethered laparoscopic probe 200. In the laparoscopic probe 200 of FIG. 2A, there is no beta radiation detector, although the skilled person would appreciate that the embodiments shown in FIGS. 1 and 2A may be combined.

The laparoscopic probe head 102 of FIG. 2A also comprises a means for facilitating the localization of a source of radiation from a radiopharmaceutical within a cavity of a subject. In the embodiment of FIG. 2A, the laparoscopic probe 200 comprises a mechanism for moving the gamma detector relative to the radiation shielding 114 to adjust the field of view of the gamma detector through the detection aperture, that is, through the void formed by the radiation shielding 114 at the detection end of the laparoscopic probe 200.

Figure 2B:
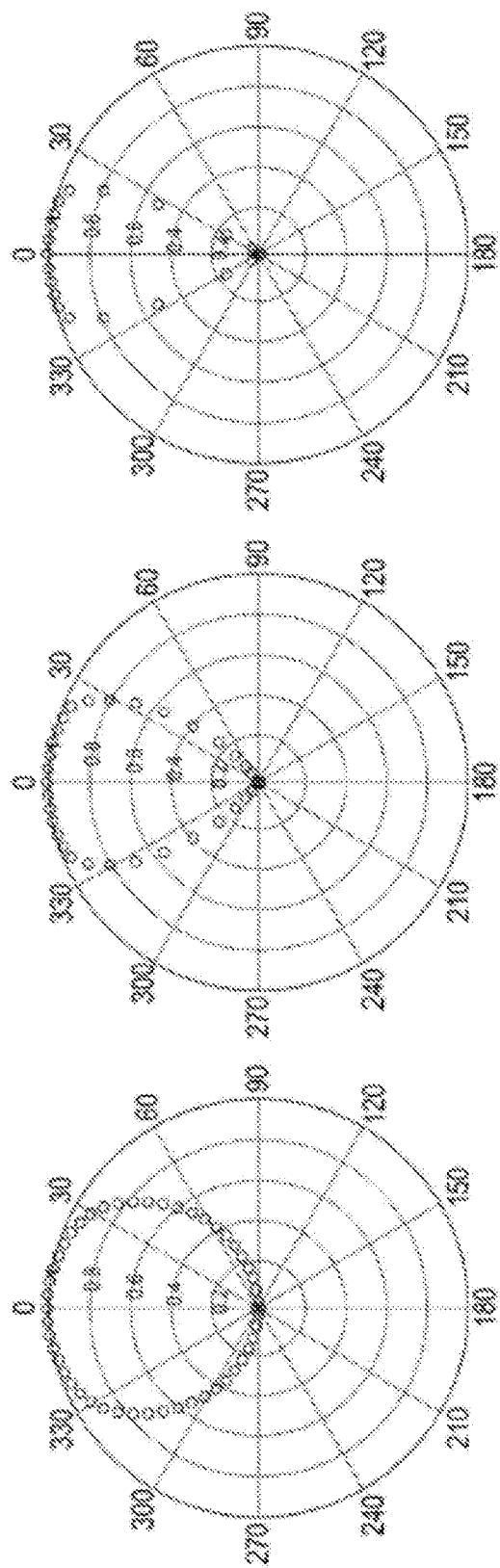
FIG. 2B shows polar plots of the angular field of view of the tethered laparoscopic probe of FIG. 2A configured in three ways.

In particular, the scintillator 110 (and photodetector 112) of FIG. 2A is moveable within the probe head 102 to adjust the field of view of the gamma radiation detector. The position of the scintillator 110 determines the field of view of the sensor as shown in FIG. 2B. The advantage of using such a mechanism in place of a collimator is that the sensitivity is not affected by additional losses due to the fill factor of the collimator. In use, it is impractical to replace a first collimator with a second collimator in order to adjust a field of view of the device—accordingly, an adjustable gamma radiation detector provides many advantages.

The sensitivity and adjustability of the laparoscopic probe 200 are particular concerns for the laparoscopic application: the outer diameter of the laparoscopic probe 200 is restricted and therefore the size of the gamma radiation detector itself is also very small, and so it is undesirable to trade-off between sensitivity and adjustability.

FIG. 2B shows polar plots showing the angular field of view for a probe with a 6 mm diameter gamma detection element, 3 mm thick combined casing 106 and side shielding 114, and 3 mm rear shielding 116. The position of the front of the scintillator 110 from the detection aperture (edge of the side shielding 114) is, from left to right, 0 mm, 3 mm, and 6 mm respectively.

The skilled person would appreciate that although, in FIG. 2, the scintillator 110 moves inside the side shielding, in an alternative embodiment, it may be the side shielding 114 that is arranged to move within the probe head such that the field of view of the detector changes. For example, the rear shielding 116 is sized such that the side shielding 114 can pass around the rear shielding to adjust the field of view of the detector.

The movement of the scintillator relevant to the side shielding 114 can be facilitated by any suitable means. For example, the mechanism for moving the gamma radiation detector relative to the radiation shielding 114 to adjust the field of view of the gamma detector through the detection aperture may comprise a latched button (such as is often found on pens). The gamma radiation detector or the side shielding 114 may be spring loaded such that, for example, the gamma radiation detector or the side shielding is initially arranged in a first position in which the gamma radiation detector has a first field of view (e.g. a wide FOV) and, on actuation of the spring loaded mechanism, the gamma radiation detector or the side shielding 114 is moved from the first position to a second position in which the gamma radiation detector has a second field of view (e.g. a narrow FOV).

As another example, the mechanism may be a screw thread. For example, the casing can be in two sections, one of which can be mechanically rotating with respect to the grip. An internal screw thread between the rotatable casing and the side shielding would translate this rotation into forward or backward movement of the shield 114. Again, it can be envisaged this can be done with a second surgical tool and that two or more stable positions are defined. To facilitate the rotation gripping features can be included on the casing (for example, two textures flats).

The embodiments described herein all allow a user to locate a source of radiation in a cavity quickly and efficiently. While some embodiments do so by using additional detectors, others do so by improved shielding against background radiation. However the embodiments described herein may be combined in any suitable way.

Due to the fixed limit on the outer diameter of the laparoscopic probe head 102 for passing through a trocar, for static radiation shielding there is a trade-off between side rejection and sensitivity as the side shielding depth/thickness constrains the size of the gamma radiation detector, for example the size of a scintillator. The inventors have recognized that to achieve a good signal it is beneficial to have a rejection ratio of >1000 and so, for example, if a trocar has a diameter of 12 mm, then for 6 mm of radiation shielding a scintillator of only 3 mm radius may be used.

Figure 3A:
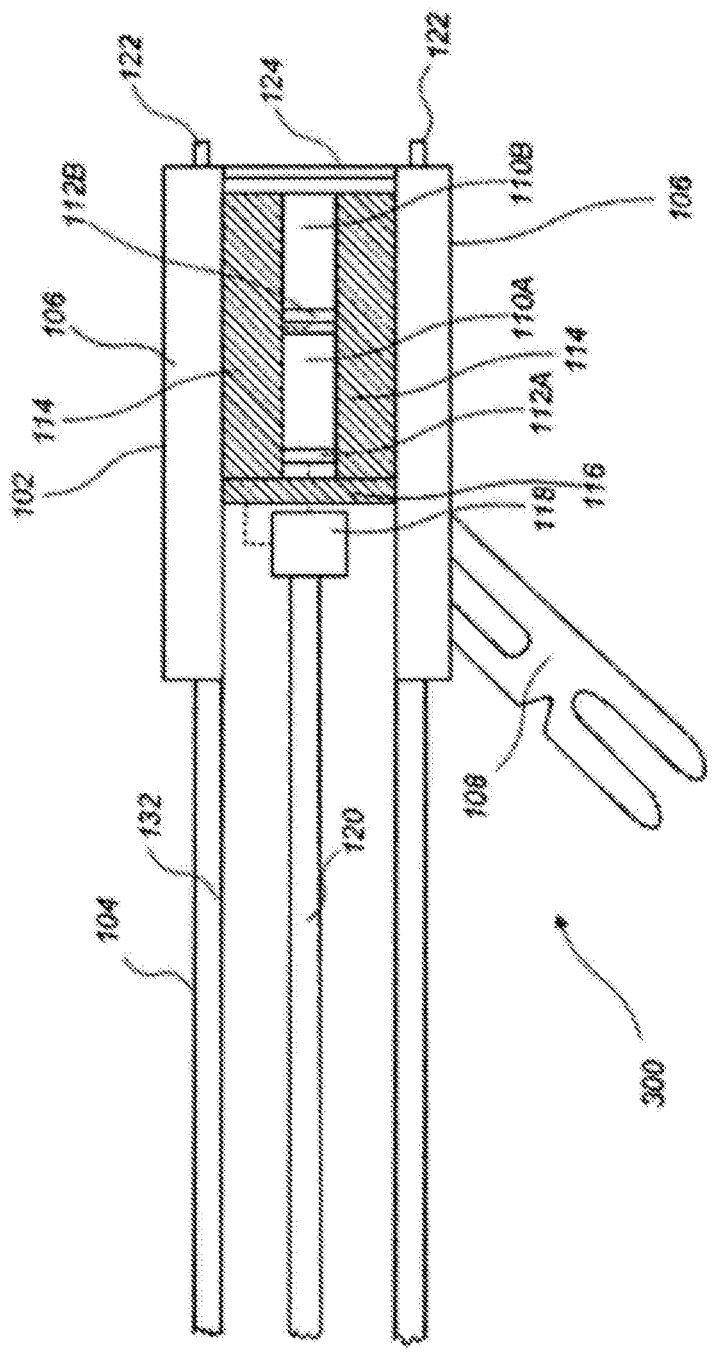
FIG. 3A illustrates a tethered laparoscopic probe according to another embodiment of the invention.

FIG. 3A shows a laparoscopic probe 300 according to another embodiment. In the embodiment shown in FIG. 3A, there are two gamma radiation detectors. In particular, the laparoscopic probe 300 comprises a first gamma radiation detector, the first gamma radiation detector comprising a first scintillator 110A and a first photodetector 112A to detect the scintillated light from the first scintillator 110A. The laparoscopic probe 300 further comprises a second gamma detector, the second gamma detector comprising a second scintillator 110B and a second photodetector 112B. The second gamma detector is located in front of the first gamma detector (that is, the second gamma radiation detector is located between the first gamma radiation detector and the detection aperture).

By providing multiple gamma radiation detectors, the signals from both gamma radiation detectors may be processed to extract further information than it is possible to determine for a single gamma radiation detector. For example, it is possible to determine additional directional information which can assist in facilitating the localization of the source of radiation. Such a dual detection system using a front gamma radiation detector and a rear gamma radiation detector therefore allows for active collimation and can provide a good compromise between the versatility and the complexity of the laparoscopic probe 300.

A key benefit of using two detection elements is that the energy resolution is enhanced due to the reduction in the aspect ratio of the sensing elements. This allows for more robust exclusion of Compton electrons away from the photopeak.

The two elements may be used to detect in coincidence to enhance specificity and collimation. This requires sophisticated time gating and reduces sensitivity. Instead, the time averaged signal from the two elements can be combined by using summation or difference. The modes have varying scaling with distance and angle. As the summation or difference counts are a form of post processing it is possible to use them concurrently and to combine the information to estimate the depth of a well localized source.

Figure 3B:
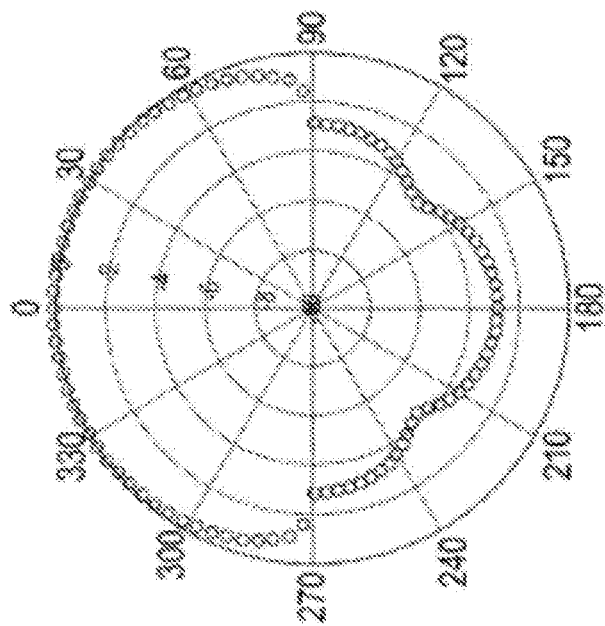
FIG. 3B shows a polar plot and a log polar plot of the angular field of view for the laparoscopic probe of FIG. 3A when signals from two gamma radiation detectors are summed.
Figure 3B:
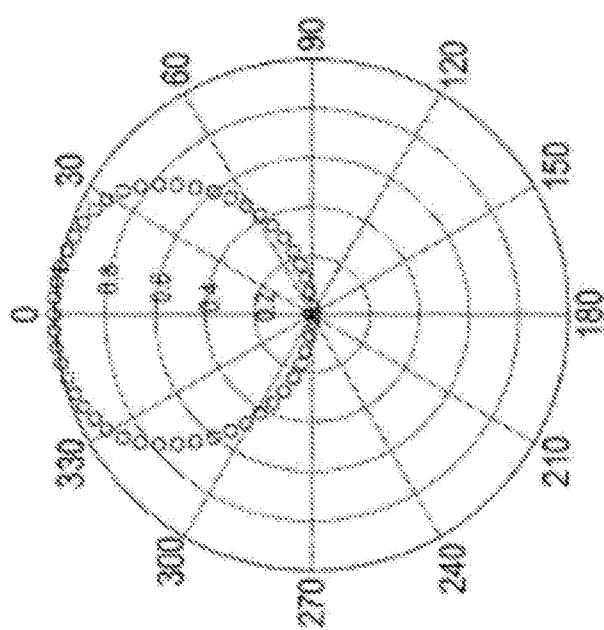

FIG. 3B shows a polar plot (left) and a log polar plot (right) of the angular field of view for a laparoscopic probe 300 having dual gamma radiation detectors when the signals from both gamma radiation detectors are combined by summation. In particular, the radiation detectors are of a similar combined size as the single gamma radiation detector described above in relation to FIG. 2A. As shown by the FIG. 3B, the angular dependence of the laparoscopic probe's field of view is unmodified from the single element design as shown in FIG. 2B, whilst maintaining the benefit of higher energy resolution. The log polar plot is provided for comparison with other modalities described herein.

The skilled person would appreciate that the first and second gamma radiation detectors may be the same size of may be of different sizes. The first and second scintillators may be the same or different.

Figure 3C:
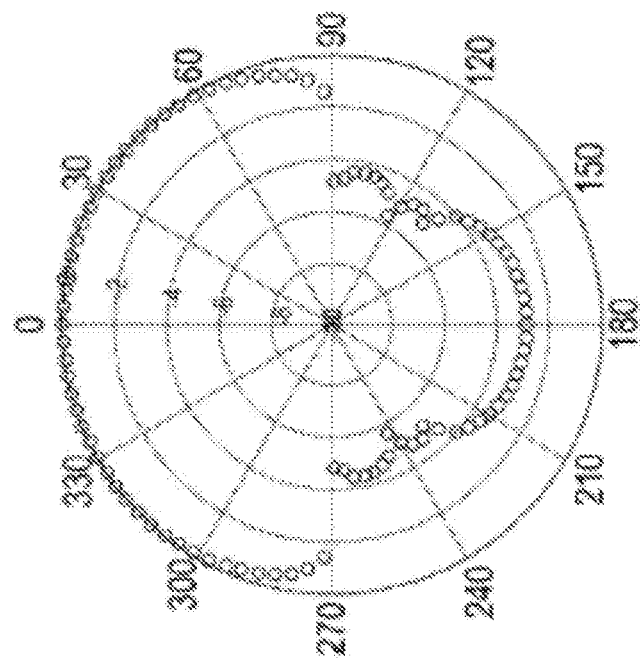
FIG. 3C shows a polar plot and a log polar plot of the angular field of view for the laparoscopic probe of FIG. 3A when signals from two gamma radiation detectors are compared.

If the difference between the counts of both gamma radiation detectors is instead calculated, this can also provide several benefits. In particular, a more uniform sensitivity across the field of view of the laparoscopic probe 300 is obtained. FIG. 3C shows a polar plot (left) for the field of view of a laparoscopic probe 300 for which the difference in the counts of the gamma radiation detectors is analyzed.

FIG. 3C also shows a log polar plot (right). As is shown by the log polar plot in FIG. 3C when compared with that of FIG. 3B, if one analyses the difference between the two gamma radiation detectors, then there is a factor of 10 improvement compared with when the counts are combined additively. This is due to the fact that noise from gamma radiation that successfully passes through the side radiation shielding 114 is largely discarded.

Figure 4A:
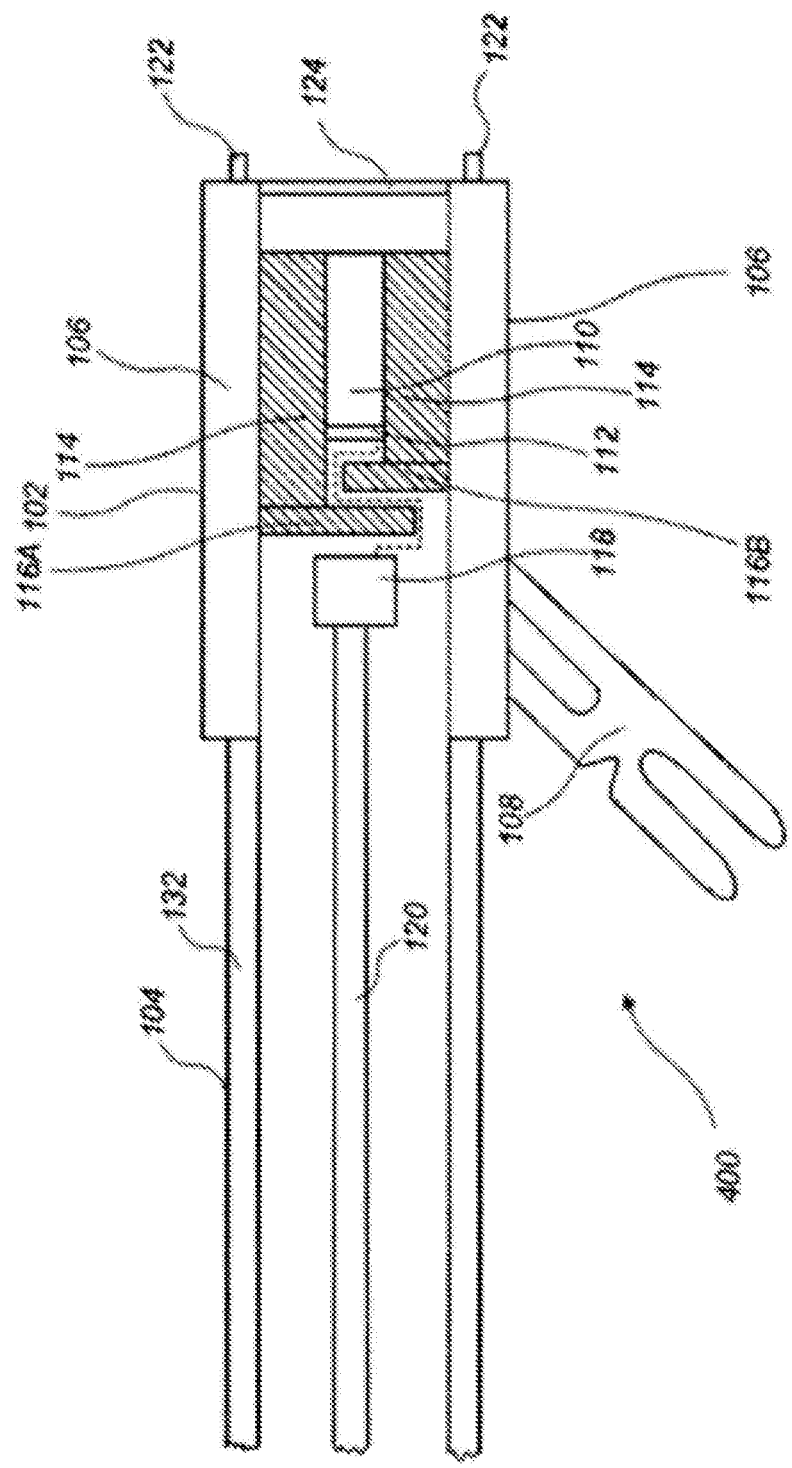
FIG. 4A illustrates a tethered laparoscopic probe according to another embodiment of the invention.

FIG. 4A shows a tethered laparoscopic probe 400 according to another embodiment. The skilled person would appreciate that the embodiment shown in FIG. 4A may be combined with each/any of the other embodiments described herein.

The tethered laparoscopic probe 400 comprises, as previously, a gamma radiation detector comprising a scintillator 110 and a photodetector 112 and radiation shielding to define a detection aperture. However, in the embodiment shown in FIG. 4A, the rear shielding comprises two layers of shielding 116A and 116B. The first layer of shielding extends inwards from a first side of the casing 106; the second layer of shielding extends inwards from a second side of the casing 106. The two layers 116A and 116B together define a tortuous path between the gamma radiation detector and the circuitry 118, along which detection signals may be communicated via a wire (illustrated by the dashed line in the figure).

The first layer of shielding 116A which extends inwards from a first side of the casing 106 is displaced relative to the second layer of shielding 116B which extends inwards from a second side of the casing 106. The two displaced layers 116A and 116B which extend from opposite sides of the casing 106 define a tortuous or sinuous path via which a wire connects the gamma radiation detector and the circuitry 118. The wire shown in FIG. 4A follows a path around the layer of shielding 116B, conforming to the shape of the shielding 116B, through to a gap formed by the two displaced layers of shielding 116A and 116B, and then follows a path around the layer of shielding 116A, conforming to the shape of the shielding 116A, through to the circuitry 118.

The skilled person would appreciate that while a tortuous path has been described by two distinct layers of shielding 116A, 116B in FIG. 4A, that a tortuous path may alternatively be formed by a single composite layer of rear shielding. Of course, further shielding layers may also be used. The tortuous path of FIG. 4A thus ensures that there is always at least one layer of shielding between the rear of the probe head and the radiation detector.

Figure 4B:
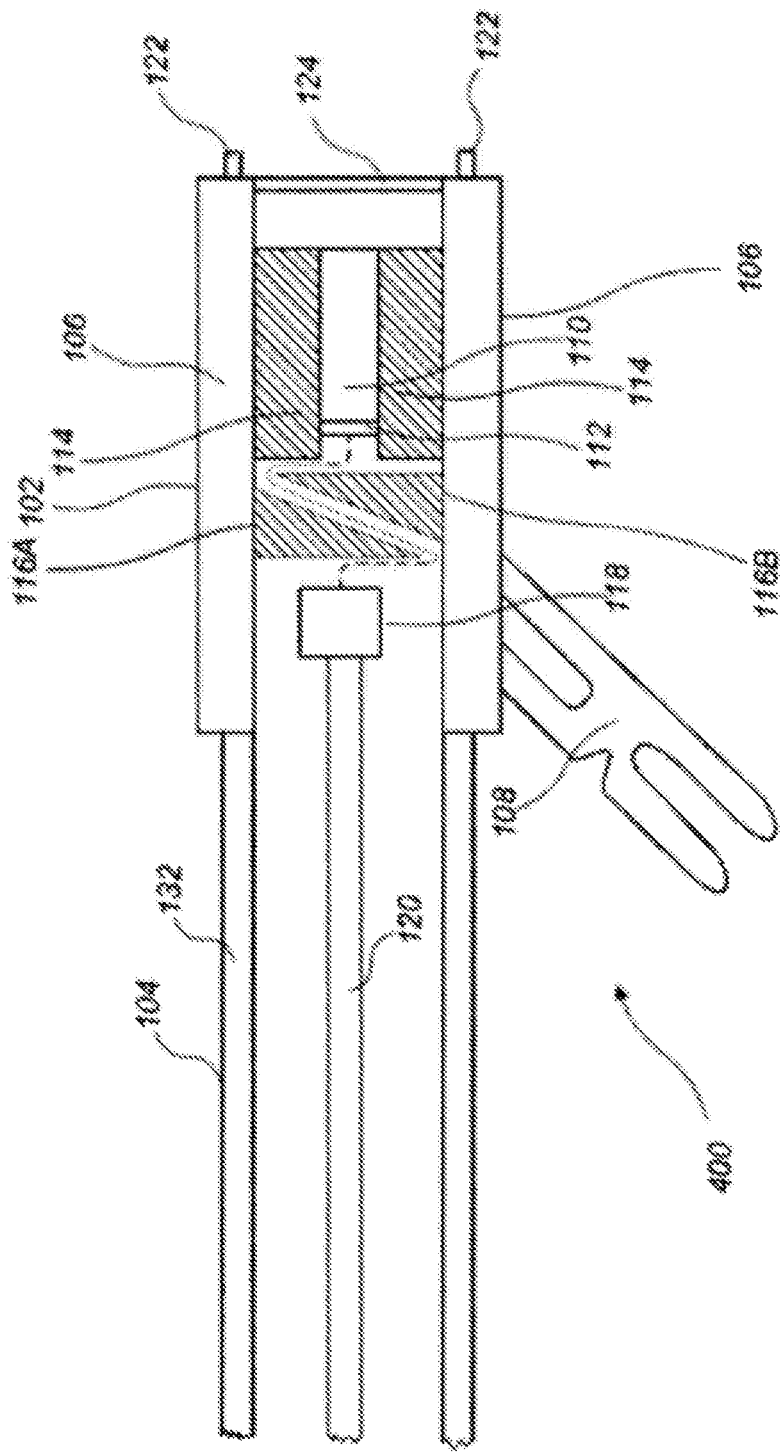
FIG. 4B illustrates a tethered laparoscopic probe according to another embodiment of the invention.

FIG. 4B shows another configuration of the shielding layers to provide a tortuous path. The tethered laparoscopic probe 400 comprises, as previously, a gamma radiation detector comprising a scintillator 110 and a photodetector 112 and radiation shielding to define a detection aperture. However, in the embodiment shown in FIG. 4B, the first layer of shielding and the second layer of shielding define a tortuous path between the gamma radiation detector and the circuitry 118, such that a wire (illustrated by the dashed line in the figure) enters the gap between the two layers of shielding 116A and 116B at an angle relative to a longitudinal axis through the tethered laparoscopic probe 400. The wire shown in FIG. 4B follows a path around the layer of shielding 116B, conforming to the shape of the shielding 116B, then enters the gap between the two layers of shielding 116A and 116B at an angle relative to a longitudinal axis through the probe and then follows a path around the layer of shielding 116A, conforming to the shape of the shielding 116A, through to the circuitry 118. The angle relative to the longitudinal axis may be 10 degrees. The angle relative to the longitudinal axis may be 15 degrees. The angle relative to the longitudinal axis may be 20 degrees. The angle relative to the longitudinal axis may be 25 degrees. The angle relative to the longitudinal axis may be 30 degrees.

The skilled person would appreciate that while a tortuous path has been described by two distinct layers of shielding 116A, 116B in FIG. 4B, that a tortuous path may alternatively be formed by a single composite layer of rear shielding. Of course, further shielding layers may also be used. Advantageously, by providing a tortuous path in the form of a substantially straight path offset from a longitudinal axis, at all points along the path, there is substantially the same amount of radiation shielding between the rear of the probe head and the radiation detector.

In the previously described embodiments, the wire between the photodetector 112 and the circuitry 118 was shown to pass through a small piercing in the rear shielding. However, by providing such a small piercing there is a chance that gamma radiation may penetrate through the resultant gap in the shielding to be detected by the gamma radiation detector. By providing a tortuous or winding path in the laparoscopic probe 400, there is no direct line of sight between the circuitry 118 and the gamma radiation detector along which gamma radiation may pass unimpeded to contribute to noisy detections. In this way, such a tortuous path allows a user to better determine a location of a radiation source by reducing noisy signals through the rear of the probe head 102.

The skilled person would appreciate that although two rear shielding layers 116A and 116B are shown in FIG. 4A and FIG. 4B, there may be further shielding layers. The shielding layers may be provided in any configuration to provide a tortuous path.

Figure 5A:
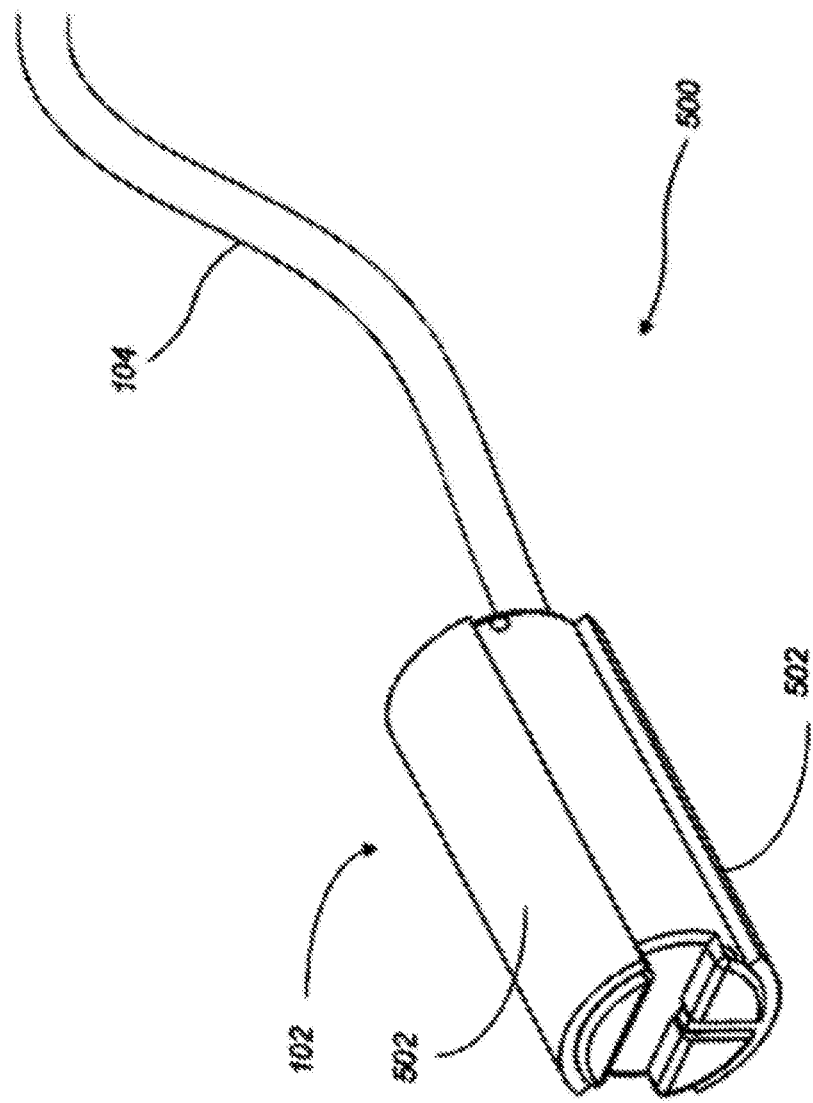
FIG. 5A illustrates a tethered laparoscopic probe according to another embodiment of the invention, with deployable shielding arranged in a deployed configuration.

FIG. 5A shows a tethered laparoscopic probe 500 according to another embodiment. The probe head 102 comprises means for, in use, facilitating the localization of a source of radiation from the radiopharmaceutical within the cavity. In particular, for the probe 500 the means comprises deployable radiation shielding 502. In FIG. 5A, the deployable radiation shielding 502 is shown in the deployed (assembled) configuration, whereby the deployable shielding 502 is arranged to inhibit radiation from passing through the side of the probe head 102. The deployable radiation shielding 502 comprises rigid, foldable sheeting. The deployable shielding 502 may be formed of any suitable material. For example, the deployable radiation shielding 502 may comprise tantalum. The deployable radiation shielding 502 may comprise tungsten (with an applied biocompatible coating).

Figure 5B:
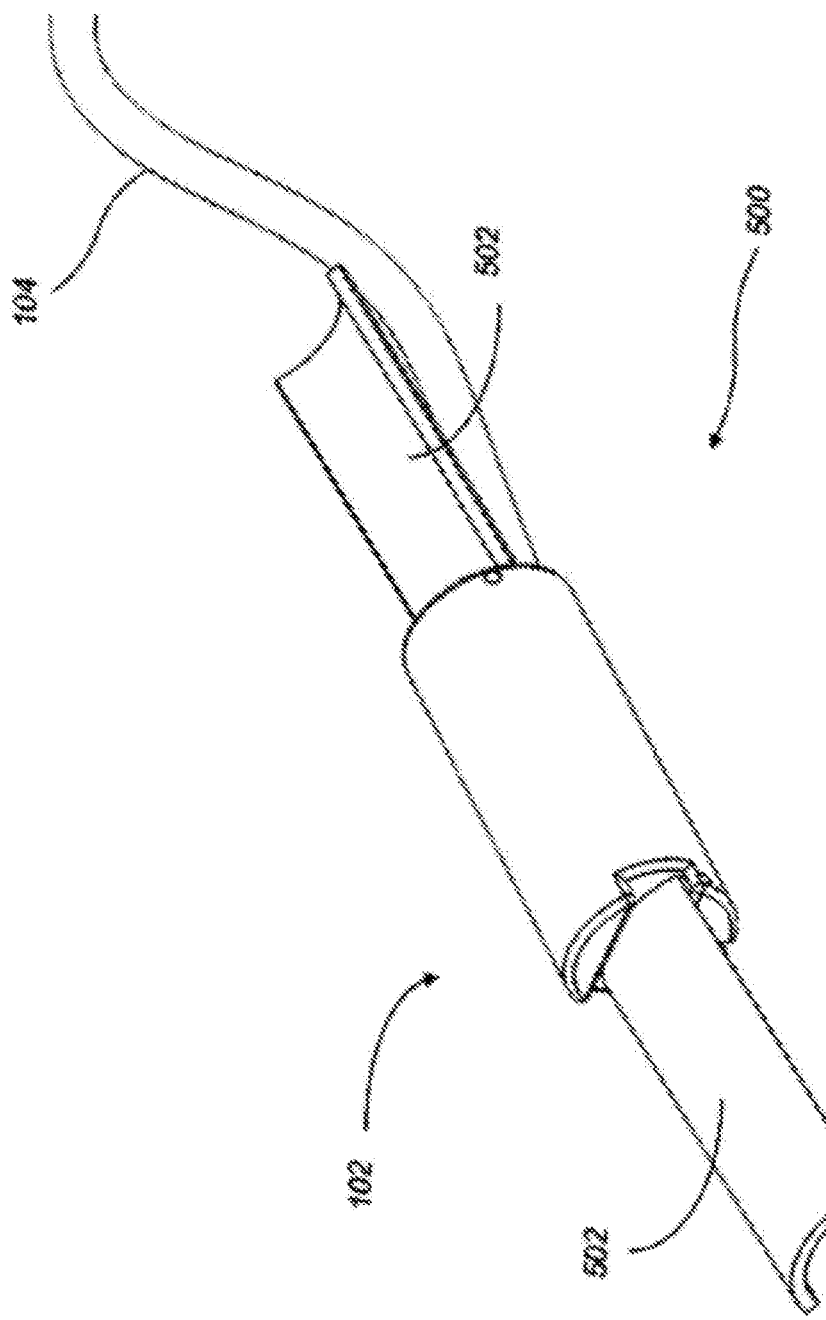
FIG. 5B illustrates the tethered laparoscopic probe of FIG. 5A with deployable shielding arranged in an undeployed configuration.

FIG. 5B shows the tethered laparoscopic probe 500 with the deployable shielding 502 in an undeployed (unassembled) configuration, wherein the shielding 502 is arranged such that the probe head is insertable through the trocar. As can be seen from FIGS. 5A and 5B, the deployable shielding 502 comprise a rigid sheeting, each sheet foldable about a pivot.

In use, the laparoscopic probe 500 may be arranged such that the deployable shielding 502 is in its undeployed configuration to pass through a trocar. Once inside the cavity, the shielding 502 can be arranged in its deployed/ assembled configuration in which the diameter of the probe head may be larger than the diameter of the trocar. By deploying the shielding 502 inside the cavity, the restriction on probe head size caused by the trocar is bypassed and a thicker layer of radiation shielding is provided in use to reduce noise. By reducing the noise caused by radiation passing through the side of the probe head, a user can better locate the source of radiation within the cavity.

The deployable shielding 502 may be assembled and/or disassembled by manipulation with surgical tools inside the cavity. Optionally, latching features may be provided to allow the deployable shielding 502 to be held securely in either the deployed configuration or the undeployed configuration or in any other configuration in between.

The rigid sheets of the deployable shielding 502 may be mechanically coupled to each other, or may be uncoupled from each other. Although two parts are shown in FIGS. 5A and 5B, the skilled person would appreciate that the deployable shielding 502 may comprise any number of layers. A cable may be attached to one or more parts of the deployable shielding 502 for communications and/or power transfer.

Figure 6A:
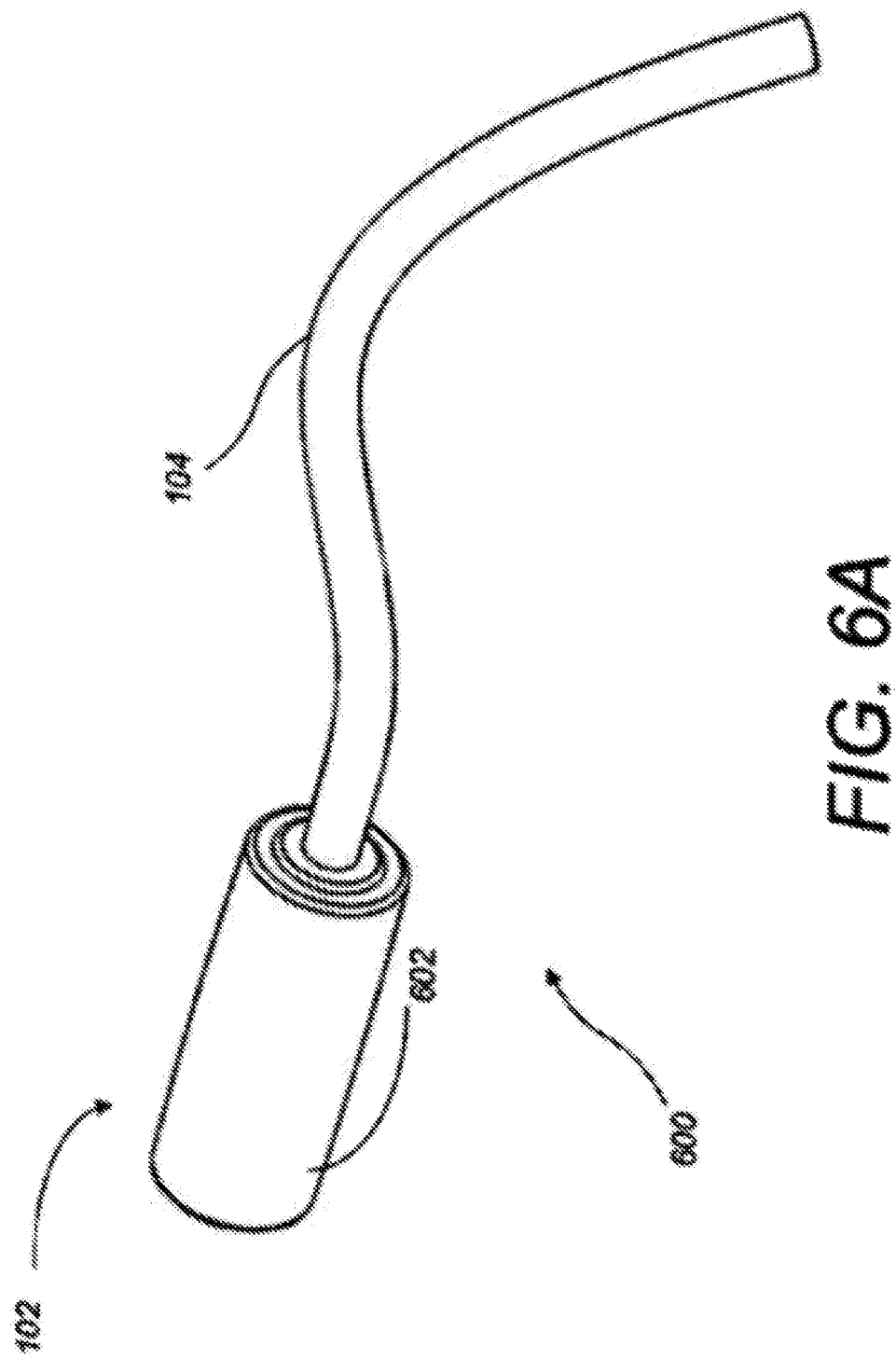
FIG. 6A illustrates a tethered laparoscopic probe according to another embodiment of the invention, with deployable shielding arranged in an undeployed configuration.
Figure 6B:
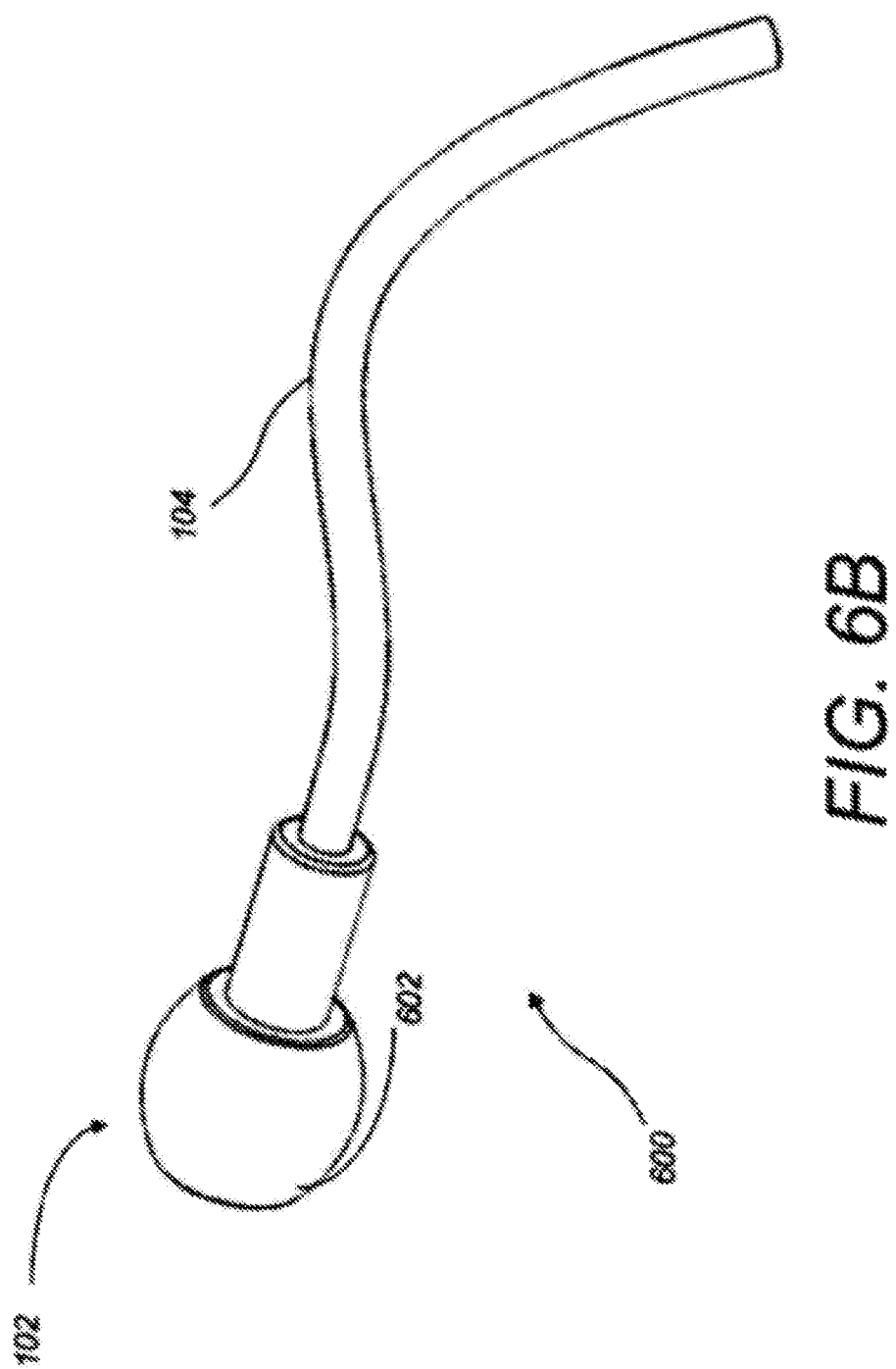
FIG. 6B illustrates the tethered laparoscopic probe of FIG. 6A with deployable shielding arranged in a deployed configuration.

FIGS. 6A and 6B show a laparoscopic probe 600 according to another embodiment which also features deployable radiation shielding. FIG. 6A shows the deployable shielding 602 in an undeployed configuration for passing the probe head 102 through a trocar, and FIG. 6B shows the deployable shielding in a deployed configuration.

The deployable shielding 602 comprises a flexible shield made from a deformable outer surface and a dense filler material, such as tungsten beads or powder. Transition between the undeployed and deployed configurations is reversible and can be actuated by the motion of a push or pull element with respect to a reference surface.

The deployed configuration shown in FIG. 6B provides enhanced isotropy compared with the planar shield shown in FIG. 5A and so the probe 600 is less sensitive to the directionality of background sources outside of the field of view of the detector end.

Figure 7:
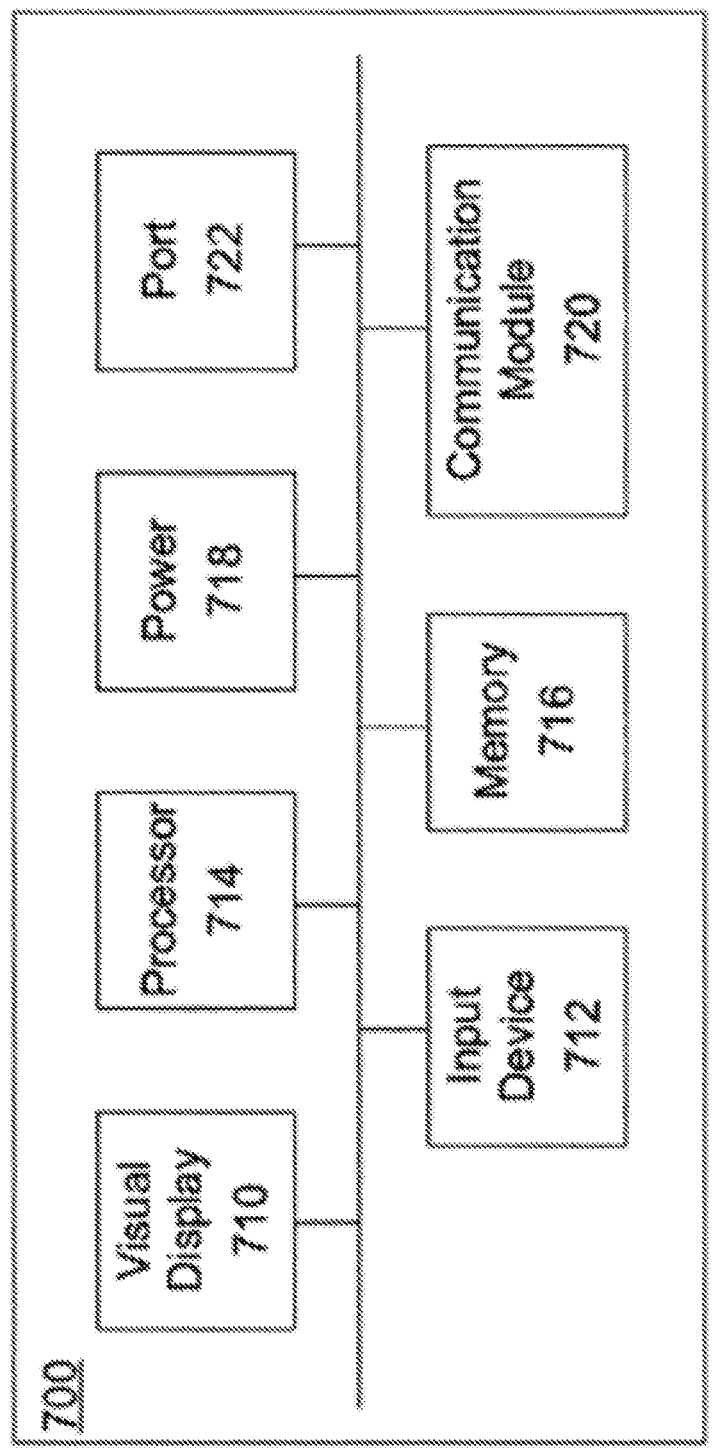
FIG. 7 is a block diagram of a computing device.

FIG. 7 is a block diagram of a computing device 700, such as may be used to receive signals from a tethered laparoscopic probe such as tethered laparoscopic probes 100, 200, 300, 400, 500 and 600 described herein. Other architectures to that shown in FIG. 7 may be used as will be appreciated by the skilled person. In some embodiments, the computing device 700 may be remote from the laparoscopic probe. In some embodiments, the computing device may in fact comprise a computing system, which may be a distributed computing system.

Referring to the figure, the computing device/controller 700 includes a number of user interfaces including visualizing means such as a visual display 710 and a virtual or dedicated user input device 712. The computing device 700 includes a processor 714, a memory 716 and a power system 718. The computing device 700 comprises a communications module 720 for sending and receiving communications between processor 714 and remote systems. For example, communications module 720 may be used to send and receive communications via a network such as the Internet. Communications module 720 may receive communications from a laparoscopic probe.

The computing device 700 comprises a port 722 for receiving, for example, a non-transitory computer readable medium containing instruction to be processed by the processor 714.

The processor 714 is configured to receive data, access the memory 716, and to act upon instructions received either from said memory 716, from communications module 720 or from user input device 712. The processor 714 may be configured to receive a detection signal from the gamma radiation detector of the tethered laparoscopic probe via circuitry 118.

The skilled person would appreciate that one or more of the components of the computing device 700 may be integrated with the laparoscopic probe. The computing device 700 may be fully integrated with probe. The computing device 700 may be remote from the probe.

Variations of the described embodiments are envisaged, for example, the features of all the described embodiments may be combined in any way.

A tether as described herein may be any suitable connection that may, in use, be used to couple a laparoscopic probe head within the cavity, through the trocar, to the outside world and may be used to, for example, withdraw the probe head from the cavity and ensure that the probe head is not misplaced within the cavity. The tether may take any suitable form, for example the tether may comprise a ribbon or cable.

It is envisaged that the term "subject" as used herein may be any suitable subject. For example, the subject may be a human or may be an animal. A cavity of the subject may comprise, for example, an abdominal cavity of the subject.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A tethered laparoscopic probe for deployment through a trocar into a cavity of a subject to detect gamma radiation from a radiopharmaceutical administered to the subject, the tethered laparoscopic probe comprising:
    a probe head shaped for insertion through the trocar and configured to be freely moveable within the cavity, the probe head comprising:
        an elongate casing comprising radiation shielding for inhibiting gamma radiation from passing through the probe head, the radiation shielding having a detection aperture for admitting gamma radiation;
        a gamma radiation detector arranged within the casing, the gamma radiation detector configured to detect gamma radiation through the detection aperture of the casing; and
    a tether coupled to the probe head and for, in use, tethering the probe head through the trocar, wherein the tether comprises a cable for communicating a signal from the gamma radiation detector from the head, and the radiation shielding comprises a tortuous path for an electrical connection through the radiation shielding to the cable to facilitate localization of a source of radiation from the radiopharmaceutical within the cavity.

2. The tethered laparoscopic probe according to claim 1, wherein the radiation shielding comprises a rear shielding, and wherein the tortuous path for the electrical connection through the radiation shielding to the cable is through the rear shielding.

3. The tethered laparoscopic probe according to claim 1, wherein the gamma radiation detector comprises: a scintillator configured to scintillate, in use, in response to received gamma radiation; and a photodetector to detect the scintillated light from the scintillator.

4. The tethered laparoscopic probe according to claim 3, wherein the photodetector comprises a silicon photomultiplier (SiPM) or an avalanche photodiode (APD).

5. The tethered laparoscopic probe according to claim 3, wherein the scintillator comprises Thallium activated Cesium Iodide, CsI:Tl.

6. The tethered laparoscopic probe according to claim 3, wherein the radiation shielding has a thickness, and the scintillator has a radius, and wherein the thickness of the radiation shielding and the radius of the scintillator are selected such that, in use, the ratio of the gamma radiation permeating through the radiation shielding of the probe head that is detected by the gamma radiation detector to the gamma radiation incident on the radiation shielding is less than or equal to 1:1000, and such that, in use, the sensitivity of the gamma radiation detector to gamma radiation incident through the detection aperture is maximized.

7. The tethered laparoscopic probe according to claim 1, wherein the gamma radiation detector comprises a semiconductor gamma radiation detector.

8. The tethered laparoscopic probe according to claim 1, further comprising a beta radiation detector arranged within the casing, between the detection aperture and the gamma radiation detector, and configured to detect beta radiation through the detection aperture of the radiation shielding.

9. The tethered laparoscopic probe according to claim 8, wherein the beta radiation detector comprises: a scintillator configured to scintillate, in use, in response to received beta radiation; and a photodetector to detect the scintillated light from the scintillator.

10. The tethered laparoscopic probe according to claim 8, wherein the tethered laparoscopic probe is arranged to communicate a composite signal, the composite signal being representative of detections of beta radiation and detections of gamma radiation.

11. The tethered laparoscopic probe according to claim 8, wherein the tethered laparoscopic probe is switchable between a first mode, in which the probe head is configured to communicate a first signal representative of a detection of gamma radiation, and a second mode, in which the probe head is configured to communicate a second signal representative of a detection of beta radiation.

12. The tethered laparoscopic probe according to claim 1, further comprising a mechanism for moving the gamma radiation detector relative to the radiation shielding to adjust the field of view of the gamma radiation detector through the detection aperture.

13. The tethered laparoscopic probe according to claim 1, wherein the gamma radiation detector comprises: a first scintillator configured to scintillate, in use, in response to received gamma radiation; and a photodetector to detect the scintillated light from the scintillator; and wherein the tethered laparoscopic probe further comprises a second scintillator configured to scintillate, in use, in response to received gamma radiation, the second scintillator arranged between the first scintillator and the detection aperture of the radiation shielding.

14. The tethered laparoscopic probe according to claim 13, further comprising a second photodetector to detect the scintillated light from the second scintillator, the second photodetector arranged between the first scintillator and the second scintillator.

15. The tethered laparoscopic probe according to claim 1, further comprising a deployable radiation shielding having a deployed configuration and an undeployed configuration; wherein, in the undeployed configuration, the deployable radiation shielding is arranged such that the probe head is insertable through the trocar; and wherein, in the deployed configuration, the deployable radiation shielding is arranged to further inhibit gamma radiation from passing through the probe head.

16. The tethered laparoscopic probe according to claim 1, wherein the tether comprises a cable for communicating a signal from the gamma radiation detector from the probe head.

17. The tethered laparoscopic probe according to claim 1, further comprising a grip for manipulating the probe head inside the cavity with a surgical tool.

18. The tethered laparoscopic probe according to claim 17, wherein the grip is beveled or wherein the grip is magnetic.

19. A tethered laparoscopic probe for deployment through a trocar into a cavity of a subject to detect gamma radiation from a radiopharmaceutical administered to the subject, the tethered laparoscopic probe comprising:
  a probe head shaped for insertion through the trocar and configured to be freely moveable within the cavity, the probe head comprising:
    an elongate casing comprising radiation shielding of a first thickness, the radiation shielding for inhibiting gamma radiation from passing through the probe head, the radiation shielding having a detection aperture for admitting gamma radiation;
    a gamma radiation detector arranged within the casing, the gamma radiation detector configured to detect gamma radiation through the detection region of the casing, the gamma radiation detector comprising: a scintillator having a radius, the scintillator configured to scintillate, in use, in response to received gamma radiation;
  and a photodetector to detect the scintillated light from the scintillator;
    wherein the thickness of the radiation shielding and the radius of the scintillator are selected such that, in use, the ratio of the gamma radiation permeating through the radiation shielding of the casing that is detected by the gamma radiation detector to the gamma radiation incident on the radiation shielding is less than or equal to 1:1000, and such that, in use, the sensitivity of the gamma radiation detector to gamma radiation incident through the detection aperture is maximized; and
  a tether coupled to the probe head and for, in use, tethering the probe head through the trocar.

20. A method for producing the tethered laparoscopic probe according to claim 19, the tethered laparoscopic probe being operable for deployment through a trocar into a cavity of a subject, the method comprising:
  selecting a radiation shielding thickness and a scintillator radius, based on a known diameter of a trocar and known radiation properties of a radiopharmaceutical when administered to the subject, such that in use the ratio of the gamma radiation permeating through the radiation shielding that is detected by the gamma radiation detector to the gamma radiation incident on the radiation shielding is less than or equal to 1:1000;
  providing an elongate casing, the elongate casing having a diameter suitable for insertion through the trocar, the casing comprising radiation shielding of the selected radiation shielding thickness;
  arranging, within the casing, a gamma radiation detector comprising: a scintillator having the selected scintillator radius, the scintillator configured to scintillate, in use, in response to received gamma radiation; and a photodetector to detect the scintillated light from the scintillator; and
  coupling a tether to the probe head.

* * * * *